United States Patent
Hanson

(10) Patent No.: US 6,457,474 B1
(45) Date of Patent: Oct. 1, 2002

(54) METHOD OF TREATING CHEST PAIN

(76) Inventor: Carl E. Hanson, P.O. Box 33427, St. Paul, MN (US) 55133-3427

( * ) Notice: Subject to any disclaimer, the term of this patent is extended or adjusted under 35 U.S.C. 154(b) by 0 days.

(21) Appl. No.: 08/903,677

(22) Filed: Jul. 31, 1997

(51) Int. Cl.[7] .............................................. A61B 19/00
(52) U.S. Cl. ...................................................... 128/898
(58) Field of Search ......................................... 128/898

(56) References Cited

PUBLICATIONS

Ram B. Singh, Mohammad A. Niaz et al., Usefulness of antioxidant vitamins in suspected acute myocardial infarction, Am. J. Cardiol. 77(4), pp. 232–236, 1996.*

Elizabeth Dapcich–Miura, Melbourne F. Hovell, Contingency management of adherence to a complex medical regiment in an elderly heart patient, Behvior Theralpy, 10(2), p. 193–201, 1979.*

R. A. Riemersma, D. A. Wood et al., Risk of angina pectoris and plasma concentrations of vitamins A, C, and E and carotene, The Lancet 337(8732), pp. 1–5, 1991.*

Heather D. Langtry, Caroline M. Spencer, Nisolpinine coat–core: a review of its pharmacodynamic and pharmacokinetic properties and clinical efficacy in the management of ischemic heart disease, Drugs, 53(5), pp. 867–884, 1997.*

* cited by examiner

*Primary Examiner*—Dinh X. Nguyen

(57) ABSTRACT

A method of alleviating chest pain that stems from the heart, which method comprises: (a) noticing a pain in the chest; and then shortly thereafter (b) taking lime juice into the body to alleviate the chest pain.

17 Claims, No Drawings

METHOD OF TREATING CHEST PAIN

TECHNICAL FIELD

This invention pertains to a method of treating chest pain, particularly angina pectoris.

BACKGROUND

Angina pectoris is a condition where a person feels paroxysmal pain in the chest. This clinical complex is characterized by various degrees of chest pain that occurs in sudden attacks. The chest pain may be accompanied by other symptoms, notably pain or discomfort of the arms, shoulders, and other sites. The symptoms are most often induced by some physical or emotional stress and often subside promptly with rest or appropriate therapy. *McGraw Hill Encycl. Sci. & Tech.,* vol. 1, p. 539 (6$^{th}$ Ed. 1987).

The chest pain typically is associated with an insufficient supply of blood to a portion of the heart. Common occurrences that precede an angina attack are changes that cause a decrease in blood supply to heart muscle or that create sudden extra demands on the heart so that there is a relative inadequacy of blood. Arteriosclerosis frequently is responsible for the narrowing or partial occlusion of one of the coronary arteries or branches, but other contributing factors such as diabetes mellitus, familial incidence, and emotional stress are examples of other disorders that may set the stage for an anginal attack. This form of coronary heart disease sometimes is a precursor to a heart attack or coronary thrombosis, where a persons artery becomes occluded by a blood clot. There is much overlap between angina pectoris and other forms of coronary heart disease such as arteriosclerotic heart disease and myocardial infarction. *McGraw Hill Encycl. Sci. & Tech.,* vol. 8, p. 346 (6$^{th}$ Ed. 1987).

Doctors regularly prescribe nitroglycerin to patients that suffer from angina pectoris. After oral administration, nitroglycerin is metabolized rapidly in the intestinal wall and liver, so that systemic bioavailability is rather low. Consequently, oral doses are quite high and plasma levels are erratic. Medical authorities do not recommend sustained-release forms of nitroglycerin because of poor oral bioavailability and favorable tolerances. *Remington's Pharmaceutical Sciences,* Chap. 41, p. 844, (18$^{th}$ Ed. 1990).

Nitroglycerin is commonly administered in the form of very small tablets that are approximately one-eight inch in diameter. These tablets are very difficult for the patient to handle: they can be easily dropped and often more than one tablet comes out of the bottle during dispensing. Size also makes it hard for the patient to return unneeded tablets to the bottle, particularly when moisture is present on the patient's hand.

When taking nitroglycerin, patients put the tablet under their tongue and wait about two-to-four minutes for the tablet to dissolve. It is sometimes not easy for the patient to ascertain if the medicine has been properly ingested. The patient then waits approximately five minutes for the angina attack to go away.

SUMMARY OF THE INVENTION

This invention provides an alternative to taking nitroglycerin to combat chest pain such as angina pectoris. In accordance with this invention, a person takes in lime juice after noticing the onset of the chest pain. As the term is used in this document, "lime juice" means lime juice or limeade or any combination that includes the juice of a lime whether in concentrated or diluted form.

The inventor surprisingly discovered that by taking lime juice shortly after noticing that he was experiencing an anginal attack that his chest pain immediately subsided. The lime juice can be easily administered by, for example, placing about one-fourth teaspoon or more of frozen concentrate lime juice in the mouth, letting it dissolve, and swallowing. The inventor also discovered that by consuming lime juice regularly, for example, by drinking about at least a glass daily in non-concentrate form, that chest pain did not occur and would not reoccur.

The present invention is advantageous in that a patient can easily determine if the medicine is properly ingested. Lime juice has a very noticeable taste that disappears after it leaves the mouth. Since the juice is regularly stored in the refrigerator or freezer, it can be quickly located by the patient, particularly at nighttime where the refrigerator light plays a helpful role. This of course is very important because time may be of the essence when experiencing angina pectoris. The patient does not have to wait two-to-four minutes for a tablet to dissolve, and there is no concern for dropping tablets on the floor. Lime juice also costs much less than nitroglycerin, which typically runs about $10 to $15 for a bottle that contains about thirty pills. Because limes are a naturally occurring product meant for digestion, patients will generally experience no side effects unless they happen to be allergic to limes.

These and other advantages of the invention are more fully described below in the detailed description of this invention.

DETAILED DESCRIPTION OF PREFERRED EMBODIMENTS

In practicing the present invention, a person who experiences or has experienced chest pain associated with a heart condition takes in lime juice to alleviate the pain. The inventor discovered that after eating only about one-fourth teaspoon of commercially available frozen concentrate for lime juice or limeade, that his chest pain subsided for two to five hours at a minimum. The inventor found it much less troublesome to ingest the lime juice as opposed to taking nitroglycerin tablets for the reasons discussed above. After learning of the benefits of lime juice, the inventor used lime juice solely without taking nitroglycerin and without fear that the chest pains would reoccur.

Although lime juice is easily administered orally, it is not beyond the scope of this invention to take it using other methods such as intravenous methods. It is important to get the lime juice into the body rapidly so that it can ultimately enter the circulatory system (in form unknown) to cause a quick recovery. The lime juice may be taken, for example, in the form of juice fresh from the lime, from frozen concentrate as indicated above, or in diluted form with the addition of water. Persons skilled in the art of purification and/or pharmacology may also locate the active ingredient(s) in the lime and administer those ingredient(s) in purified form or otherwise to persons who suffer from chest pain such as angina pectoris. As lime juice is defined above it is intended to include all these forms of administering lime juice.

The inventor discovered that approximately one fourth or more teaspoons of lime juice in frozen concentrated form was sufficient to alleviate the chest pain he was suffering as a result of angina pectoris. Preferably, at least one half teaspoon was consumed to recover from an angina attack. When chest pain is strong, 2 to 3 teaspoons administered orally would remove the pain. The inventor also discovered that by drinking at least a cup of lime juice in non-concentrated form, more preferably two to five cups daily (two to three cups my be sufficient), that the chest pain did not occur or reoccur. When used in non-concentrated form approximately 16 fluid ounces to 72 fluid ounces of water are added to the frozen concentrate, which may be purchased in the store, e.g., Minute Maid™ concentrated Limeade. The manufacturer recommends the addition of about 52 fluid ounces. When lime juice is prepared from juice squeezed from a lime, the lime juice is preferably diluted at about ¼ to 2 cups of water per teaspoon of lime juice. The amount of lime juice taken may vary from person-to-person. Person should be able to determine for themselves the "effective amount" of lime juice that needs to be taken. By "effective amount" is meant an amount sufficient to have a beneficial effect on the heart after noticing the chest pain.

The following Examples have been selected to further illustrate features, advantages, and other details of the invention. It is to be expressly understood, however, that while the Example serve this purpose, the particular ingredients and amounts used as well as other conditions and details are not to be construed in a manner that would unduly limit the scope of this invention.

EXAMPLE

Example 1

Although lime juice is easily administered orally, it is not beyond the scope of this invention to take it using other methods such as intravenous methods. It is important to get the lime juice into the body rapidly so that it can ultimately enter the circulatory system (in form unknown) to cause a quick recovery. The lime juice may be taken, for example, in the form of juice fresh from the lime, from frozen concentrate as indicated above, or in diluted form with the addition of water. Persons skilled in the art of purification and/or pharmacology may also locate the active ingredient(s) in the lime and administer those ingredient(s) in purified form or otherwise to persons who suffer from chest pain such as angina pectoris.

Example 2

Limeade in non-concentrated form was prepared by opening a can of the Minute Maid™ brand Premium All Natural Frozen Concentrate for Limeade, removing the contents and placing it in a pitcher, adding approximately 52 fluid ounces (about 4.5 cans) of tap water to the frozen concentrate, and stirring. The pitcher was placed in the refrigerator so that the contents would cool. I drank approximately 2 to 3 glasses of limeade daily and did not notice the reoccurrence of chest pain.

Example 3

I purchased whole limes from the grocery store (key limes I believe). The limes were cleaned, sliced, and squeezed. I consumed approximately 1 teaspoon of the fresh-squeezed lime juice shortly after noticing the onset of chest pain. Shortly thereafter the chest pain subsided.

This invention may take on various modifications and alterations without departing from the spirit and scope thereof. Accordingly, it is to be understood that this invention is not to be limited to the above-described, but it is to be controlled by the limitations set forth in the following claims and any equivalents thereof. It is also to be understood that this invention may be suitably practiced in the absence of any element not specifically disclosed herein.

What is claimed is:

1. A method of preventing the reoccurrence of chest pain associated with the heart, which method comprises:
   (a) noticing a pain in the chest; and then shortly thereafter
   (b) taking an effective amount of lime juice into the body to alleviate the chest pain.

2. The method of claim 1, wherein the chest pain is angina pectoris.

3. The method of claim 1, wherein the lime juice enters the body by consuming it orally.

4. The method of claim 2, wherein the lime juice is consumed in concentrated form by taking at least one half teaspoon of frozen concentrated lime juice or limeade.

5. The method of claim 1, further comprising:
   preventing the reoccurrence of chest pain by taking lime juice into the body daily.

6. The method of claim 5, wherein at least one cup of lime juice is consumed orally daily.

7. The method of claim 6, wherein 2 to 5 cups are consumed daily.

8. The method of claim 6, wherein 2 to 3 cups are consumed daily.

9. A method of treating angina pectoris, which method comprises:
   (a) noticing the onset of an angina attack; and then shortly thereafter
   (b) taking an effective amount of lime juice into the body.

10. The method of claim 9, wherein the lime juice is taken orally.

11. The method of claim 10, wherein the lime juice is essentially pure lime juice.

12. The method of claim 10, wherein the lime juice is frozen concentrate for limeade.

13. The method of claim 10, wherein the lime juice is limeade.

14. The method of claim 1, wherein the lime juice is administered in concentrated form.

15. The method of claim 1, wherein the lime juice is administered in the form of its active ingredients.

16. The method of claim 9, wherein the lime juice is administered in concentrated form.

17. The method of claim 9, wherein the lime juice is administered in the form of its active ingredients.

* * * * *

UNITED STATES PATENT AND TRADEMARK OFFICE
CERTIFICATE OF CORRECTION

PATENT NO. : 6,457,474 B1 Page 1 of 1
APPLICATION NO. : 08/903677
DATED : October 1, 2002
INVENTOR(S) : Carl E. Hanson It is certified that error appears in the above-identified patent and that said Letters Patent is hereby corrected as shown below:

<u>Title Page</u>
The Inventor's address is incorrect. Please delete "P.O. Box 33427, St. Paul, MN (US) 55133-3427" and insert therefore --Lanark Village, FL--.

Signed and Sealed this

Eleventh Day of July, 2006

JON W. DUDAS
*Director of the United States Patent and Trademark Office*

(12) EX PARTE REEXAMINATION CERTIFICATE (5405th)
United States Patent
Hanson

(10) Number: US 6,457,474 C1
(45) Certificate Issued: Jun. 13, 2006

(54) METHOD OF TREATING CHEST PAIN

(75) Inventor: Carl E. Hanson, P.O. Box 33427, St. Paul, MN (US) 55133-3427

(73) Assignee: Carl E. Hanson, Lanark Village, FL (US)

Reexamination Request:
No. 90/006,527, Feb. 10, 2003

Reexamination Certificate for:
Patent No.: 6,457,474
Issued: Oct. 1, 2002
Appl. No.: 08/903,677
Filed: Jul. 31, 1997

(51) Int. Cl.
*A61B 19/00* (2006.01)

(52) U.S. Cl. ..................................................... 128/898
(58) Field of Classification Search ........................ None
See application file for complete search history.

(56) References Cited

PUBLICATIONS

Riemersma et al. 1991. Risk of Angina Pectoris and Plasma Concentrations of Vitamins A, C, E, and Carotene. The Lancet. vol. 337, pp. 1–5.*

Singh et al. 1996. Usefulness of Antioxidant Vitamins in Suspected Acute Myocardial Infarction. Ind. J. Exp. Infarct Survival. vol. 77, pp. 232–236.*

Internet reference titled "International Recipes Online", www.simpleinternet.com (first published online in 1995), 1 page.*

Internet reference titled "Vitamin C and Scurvy", www.u-mass.edu (from a 1991 publication by Hamilton et al entitled "Nutrition: Concepts and Controversies", New York: West Publishing Co.), 1 page.*

Symbio's Food Effects Index, www.symbios–witticism–page.com (1998).*

Heart Health, www.heathglimpses.com (2000).*

* cited by examiner

*Primary Examiner*—C. R. Tate

(57) ABSTRACT

A method of alleviating chest pain that stems from the heart, which method comprises: (a) noticing a pain in the chest; and then shortly thereafter (b) taking lime juice into the body to alleviate the chest pain.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 46–60:

Although lime juice is easily administered orally, it is not beyond the scope of this invention to take it using other methods such as intravenous methods. It is important to get the lime juice into the body rapidly so that it can ultimately enter the circulatory system (in form unknown) to cause a quick recovery. The lime juice may be taken, for example, in the form of juice fresh from the lime, from frozen concentrate as indicated above, or in diluted form with the addition of water. Persons skilled in the art of purification and/or pharmacology may also locate the active ingredient(s) in the lime and administer those ingredient(s) in purified form or otherwise to persons who suffer from chest pain such as angina pectoris. [As lime juice is defined above it is intended to include all these forms of administering lime juice.]

Column 3, lines 29–40:

[Although lime juice is easily administered orally, it is not beyond the scope of this invention to take it using other methods such as intravenous methods. It is important to get the lime juice into the body rapidly so that it can ultimately enter the circulatory system (in form unknown) to cause a quick recovery. The lime juice may be taken, for example, in the form of juice fresh from the lime, from frozen concentrate as indicated above, or in diluted form with the addition of water. Persons skilled in the art of purification and/or pharmacology may also locate the active ingredient(s) in the lime and administer those ingredient(s) in purified form or otherwise to persons who suffer from chest pain such as angina pectoris.]

*Upon noticing a pain in my chest, I placed one-half to one teaspoon of Premium All Natural Frozen Concentrate For Limeade, Minute Maid™ brand, (contains 14 percent lime juice) onto a spoon. The spoon was placed in my mouth, and the frozen concentrated limeade dissolved and was swallowed. The chest pain subsided almost instantaneously.*

AS A RESULT OF REEXAMINATION, IT HAS BEEN DETERMINED THAT:

Claims 1–17 are cancelled.

[1. A method of preventing the reoccurrence of chest pain associated with the heart, which method comprises:
  (a) noticing a pain in the chest; and then shortly thereafter
  (b) taking an effective amount of lime juice into the body to alleviate the chest pain.]

\* \* \* \* \*